(12) United States Patent
Marks

(10) Patent No.: US 10,231,635 B1
(45) Date of Patent: Mar. 19, 2019

(54) IMPEDANCE PLETHYSMOGRAPH USING CONCURRENT PROCESSING

(71) Applicant: Lloyd A. Marks, Westfield, NJ (US)

(72) Inventor: Lloyd A. Marks, Westfield, NJ (US)

(*) Notice: Subject to any disclaimer, the term of this patent is extended or adjusted under 35 U.S.C. 154(b) by 21 days.

(21) Appl. No.: 15/256,076

(22) Filed: Sep. 2, 2016

Related U.S. Application Data

(63) Continuation of application No. 14/836,493, filed on Aug. 26, 2015, now abandoned.

(51) Int. Cl.
| | | |
|---|---|---|
| *A61B 5/00* | (2006.01) |
| *A61B 5/0295* | (2006.01) |
| *A61B 5/0432* | (2006.01) |
| *A61B 5/044* | (2006.01) |
| *A61B 5/0452* | (2006.01) |

(52) U.S. Cl.
CPC .......... *A61B 5/0295* (2013.01); *A61B 5/0006* (2013.01); *A61B 5/044* (2013.01); *A61B 5/0432* (2013.01); *A61B 5/0452* (2013.01)

(58) Field of Classification Search
CPC .............. A61B 5/02427; A61B 5/0017; A61B 5/02154; A61B 5/0261; A61B 5/1079; A61B 5/1455
See application file for complete search history.

(56) References Cited

U.S. PATENT DOCUMENTS

| | | | |
|---|---|---|---|
| 3,149,627 A | 9/1964 | Bagno | |
| 3,570,474 A | 3/1971 | Jonson | |
| 3,742,936 A | 7/1973 | Blanie et al. | |
| 3,835,839 A | 9/1974 | Brown | |
| 3,835,840 A | 9/1974 | Mount | |
| 3,847,142 A | 11/1974 | Williams, Jr. et al. | |
| 4,204,545 A | 5/1980 | Yamakoshi | |
| 4,205,688 A | 6/1980 | Hauser et al. | |
| 4,258,720 A | 3/1981 | Flowers | |
| 4,432,374 A | 2/1984 | Osanai | |
| 4,437,469 A | 3/1984 | Djordjevich et al. | |
| 4,548,211 A * | 10/1985 | Marks .................. | A61B 5/0456 600/506 |
| 5,025,784 A * | 6/1991 | Shao .................... | A61B 5/0535 600/513 |
| 7,887,491 B2 * | 2/2011 | Marks ................ | A61B 5/02141 600/485 |

* cited by examiner

*Primary Examiner* — Paula J Stice
(74) *Attorney, Agent, or Firm* — Blank Rome LLP

(57) ABSTRACT

A system and method for measuring the impedance and impedance changes in a body segment are disclosed. By utilizing an ECG buffer, at least one plethysmograph buffer, and concurrently performing at least extraction of an ECG waveform stored in the ECG buffer and extraction of impedance waveforms stored in the at least one plethysmograph buffer, enhanced signal-to-noise ratios of output signals of impedance plethysmographs are achieved. In an embodiment, improved waveform selection using template matching is also achieved. With template matching, a new candidate waveform is compared in shape to the previous average waveform and may be accepted for current averaging based on the comparison.

26 Claims, 6 Drawing Sheets

IMPEDANCE PLETHYSMOGRAPH USING CONCURRENT PROCESSING

CROSS-REFERENCE TO RELATED APPLICATIONS

This is a Continuation of application Ser. No. 14/836,493 filed Aug. 26, 2016, the contents of which application are incorporated herein by reference.

FIELD OF THE INVENTION

Embodiments are in the field of impedance plethysmography. More particularly, embodiments disclosed herein relate to systems and methods for enhancing output signals of impedance plethysmographs via concurrent processing which, inter alia, foster enhanced signal-to-noise ratios of output signals of impedance plethysmographs.

BACKGROUND OF THE INVENTION

Pulsatile volume and pulsatile flow (pulsatile volume times heart rate) in an extremity can be measured with an admittance (or equivalently an impedance) plethysmograph such as that described in U.S. Pat. No. 4,548,211. In that device, an admittance signal is derived from a body segment and QRS complexes of the patient's ECG are stored. Using the ECG as a gating signal, the admittance waveforms are averaged to reduce noise. In the device described in U.S. Pat. No. 4,548,211, this is accomplished in a linear sequence. First, a QRS complex is detected. Then an admittance waveform is captured. Then, it is determined if the captured waveform remains within certain bounds. This is done to eliminate noisy waveforms. If a waveform is accepted, it is then averaged with a number (determined by the user) of prior waveforms to produce an averaged composite waveform which has considerably less noise than the individual waveforms. The averaged waveform is then measured to determine its amplitude. The waveform and its amplitude are then displayed.

These operations are executed sequentially. The beat selection, averaging process, waveform measurement and display take a sufficiently long time such that only about 1 in 3 or 1 in 4 waveforms can be captured for averaging. This means that it takes a long time for the pulse volume readouts to appear and to be updated. Also, plethysmographic waveform amplitude varies with respiration. If the respiratory cycle is close to the frequency of intermittent plethysmographic waveform selection, then errors will be introduced.

Thus, it is desirable to provide a system and method for enhancing output signals of an impedance plethysmograph via concurrent processing which are able to overcome the above disadvantages.

It is the purpose of this invention to speed up the process so that all waveforms can be used. This is accomplished by storing the entire impedance waveform and the entire ECG waveform in buffers. The waveform extraction is then performed using the waveforms stored in the buffers. This is accomplished by using a concurrent processing software technique which allows all waveforms to be used. Waveform extraction, selection, averaging, measurement and display are performed concurrently.

This results in a marked increase in speed of acquisition. The specific means by which this is accomplished is described in the detailed description of the invention below.

It is another purpose of this invention to provide improved waveform selection using template matching. Currently, waveforms are rejected based on amplitude and amplitude of first derivative criteria only. This often permits distorted waveforms to be inappropriately accepted for averaging. With template matching, a new "candidate" waveform is compared in shape to the current averaged waveform. If it matches well, the new candidate waveform is accepted for averaging. If not, it is discarded. The specific means by which this is accomplished is described in the detailed description of the invention below.

In view of the foregoing, it should be apparent that there still exists a need for an improved impedance plethysmograph in which accuracy is improved because, in the state of the art impedance plethysmograph, not all cardiac cycles are used in the averaging process and because distorted waveforms are often inappropriately included in the averaged waveform.

More particularly, it is an object of an embodiment of this invention to use concurrent processing to acquire electrocardiographic waveforms, acquire impedance plethysmographic waveforms, to use these waveforms to select plethysmographic waveforms as candidates for averaging, to compute the average of these waveforms, to calculate the pulse volume changes corresponding to the impedance changes, to measure the amplitude of the waveforms, to compute the product of heart rate and plethysmographic waveform amplitude, to display the averaged waveform and to display updated trend lines showing the amplitudes of the pulse volume waveform and the pulse volume times heart rate product waveform.

Furthermore, it is an object of an embodiment of this invention to use template matching to improve the selection of new candidate plethysmographic waveforms for averaging. The shape of a new candidate waveform is compared to the current running averaged waveforms using a cross-correlation technique. If the shape is sufficiently similar to the running average, it is accepted for averaging. If not, it is rejected.

SUMMARY OF THE INVENTION

Embodiments are directed to a method for measuring the impedance and impedance changes in a body segment. The method comprises: acquiring an ECG waveform; detecting QRS complexes from the ECG waveform; storing the ECG waveform in at least one ECG buffer; acquiring a plurality of impedance waveforms; storing the plurality of impedance waveforms in at least one plethysmograph buffer; extracting the ECG waveform stored in the at least one ECG buffer; extracting the plurality of impedance waveforms stored in the at least one plethysmograph buffer, wherein extracting the ECG waveform and extracting the plurality of impedance waveforms are performed concurrently; and averaging the plurality of impedance waveforms to obtain a single waveform representative of the average of the plurality of impedance waveforms.

In an embodiment, the acquiring the ECG waveform, the detecting QRS complexes, the storing the ECG waveform, the acquiring the plurality of impedance waveforms, the storing the plurality of impedance waveforms, the extracting the ECG waveform, the extracting the plurality of impedance waveforms, and the averaging the plurality of impedance waveforms are performed concurrently.

In an embodiment, the method further comprises measuring the single waveform to determine its amplitude. The method may further comprise displaying the single waveform and its amplitude. The averaging the plurality of impedance waveforms, the measuring the single waveform, and the displaying the single waveform may be performed concurrently.

In an embodiment, the method further comprises comparing in shape a candidate waveform to the single waveform, wherein upon acceptance for averaging of the candidate waveform, the candidate waveform is averaged with prior accepted impedance waveforms that form the single waveform to obtain a new single waveform representative of the average of the prior accepted impedance waveforms and the candidate waveform.

In an embodiment, the method further comprises determining pulse volume from the single waveform.

In an embodiment, the averaging is performed via utilizing the QRS complexes as a gating signal.

Embodiments are also directed to a system that measures the impedance and impedance changes in a body segment. The system includes similar features that correspond to the above-mentioned method.

BRIEF DESCRIPTION OF THE DRAWINGS

The detailed description will refer to the following drawings, wherein like numerals refer to like elements, and wherein.

DETAILED DESCRIPTION OF THE INVENTION

Figure 1:
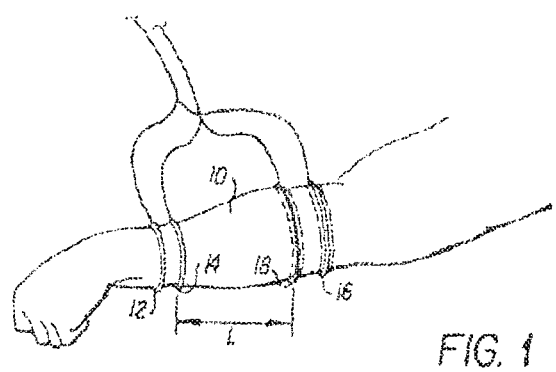
FIG. 1 is a schematic diagram illustrating an embodiment of four electrodes positioned on a human limb.

It is to be understood that the figures and descriptions of the present invention may have been simplified to illustrate elements that are relevant for a clear understanding of the present invention, while eliminating, for purposes of clarity, other elements found in a typical plethysmograph or typical method of using a plethysmograph. Those of ordinary skill in the art will recognize that other elements may be desirable and/or required in order to implement the present invention. However, because such elements are well known in the art, and because they do not facilitate a better understanding of the present invention, a discussion of such elements is not provided herein. It is also to be understood that the drawings included herewith only provide diagrammatic representations of the presently preferred structures of the present invention and that structures falling within the scope of the present invention may include structures different than those shown in the drawings. Reference will now be made to the drawings wherein like structures are provided with like reference designations.

The present disclosure hereby incorporates by reference herein the disclosure of U.S. Pat. No. 4,548,211 which was issued to Lloyd A. Marks, the inventor of the present application.

Embodiments overcome the problems described above. Embodiments address the above problems and improve the state of the art by speeding up the process so that all waveforms can be used. This is accomplished by storing the entire impedance waveform and the entire ECG waveform in buffers. The waveform extraction is then performed using the waveforms stored in the buffers. That is accomplished by using concurrent processing which allows all waveforms to be used. Waveform extraction, selection, averaging, measurement and display are performed at the same time.

This results in a marked increase in speed of acquisition and increased accuracy. The respiratory cycle causes the amplitude of the plethysmographic waveform to vary. With inspiration, the amplitude of the waveform decreases and with expiration it increases. If, for example, the device captures only one in three cycles, those cycles may coincide with the respiratory cycle, for example, that occurs during expiration. This would result in overestimation of the average pulse volume amplitude. The specific means by which this is accomplished is described below.

Additional embodiments provide improved waveform selection using template matching. In this method, a new "candidate" waveform is compared in shape to the current averaged waveform. If it matches well, it is accepted for averaging. If not, it is discarded. With the current embodiment, a "junk" waveform may still meet the amplitude criteria for acceptance. This results in corruption of the average. By using template matching the likelihood of accepting a "real" waveform is dramatically improved. The specific means by which this is accomplished is described below.

With reference to FIG. 1, one of the peripheral limbs or body segments 10 of a human body is shown, for example, the forearm. An electrical signal, of, for instance, 20 kilohertz at 1 milliamp of current, is applied to the forearm via two electrodes 12 and 16. The resultant voltage in the limb is measured between a second pair of electrodes 14 and 18 placed within the first pair of electrodes 12 and 16. The distance L between the inner electrodes 14 and 18 may be approximately 13 centimeters. All of the electrodes 12, 14, 16 and 18 may be of the circumferential type, and may consist of braided stainless steel sleeve over rubber cord attached to fleece-backed neoprene. Other types of electrodes can be used such as those described in U.S. Pat. No. 8,019,401 where a variety of such electrodes is described.

Figure 2:
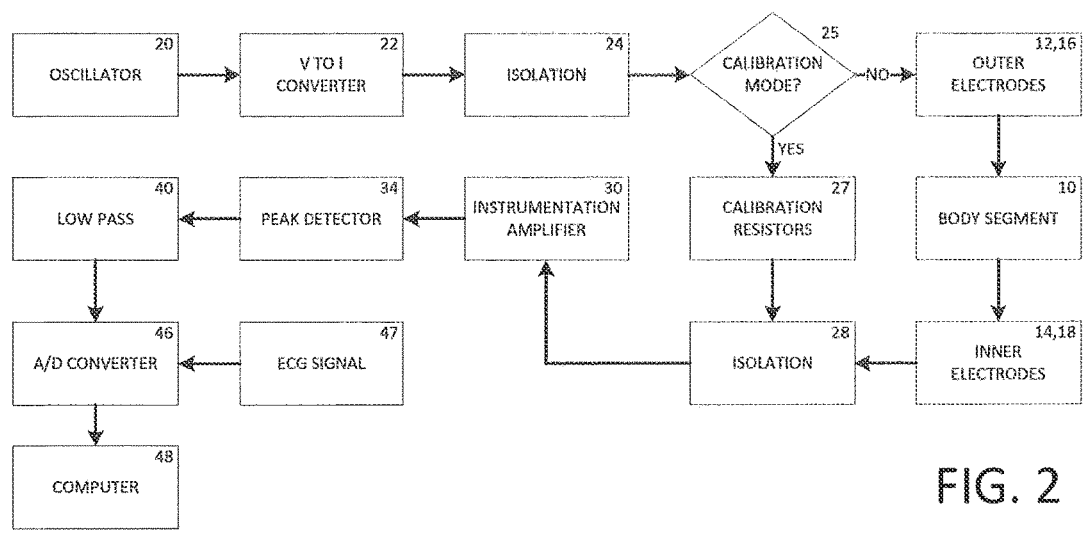
FIG. 2 is a block diagram illustrating a preferred embodiment of a peripheral limb blood flow measuring device of the present invention.

Turning now to FIG. 2, there is shown that the two outer electrodes 12 and 16 may be connected to the secondary of an isolation transformer 24, the primary of which is driven by a current source or oscillator 20, through a voltage-to-current converter 22. The two inner electrodes 14 and 18 may be connected to the primary of a second isolation transformer 28. The secondary windings of isolation transformer 28 are connected to an instrumentation amplifier 30. Each electrode 12, 14, 16 and 18 may be connected directly to its respective isolation transformers 24 and 28.

Figure 3:
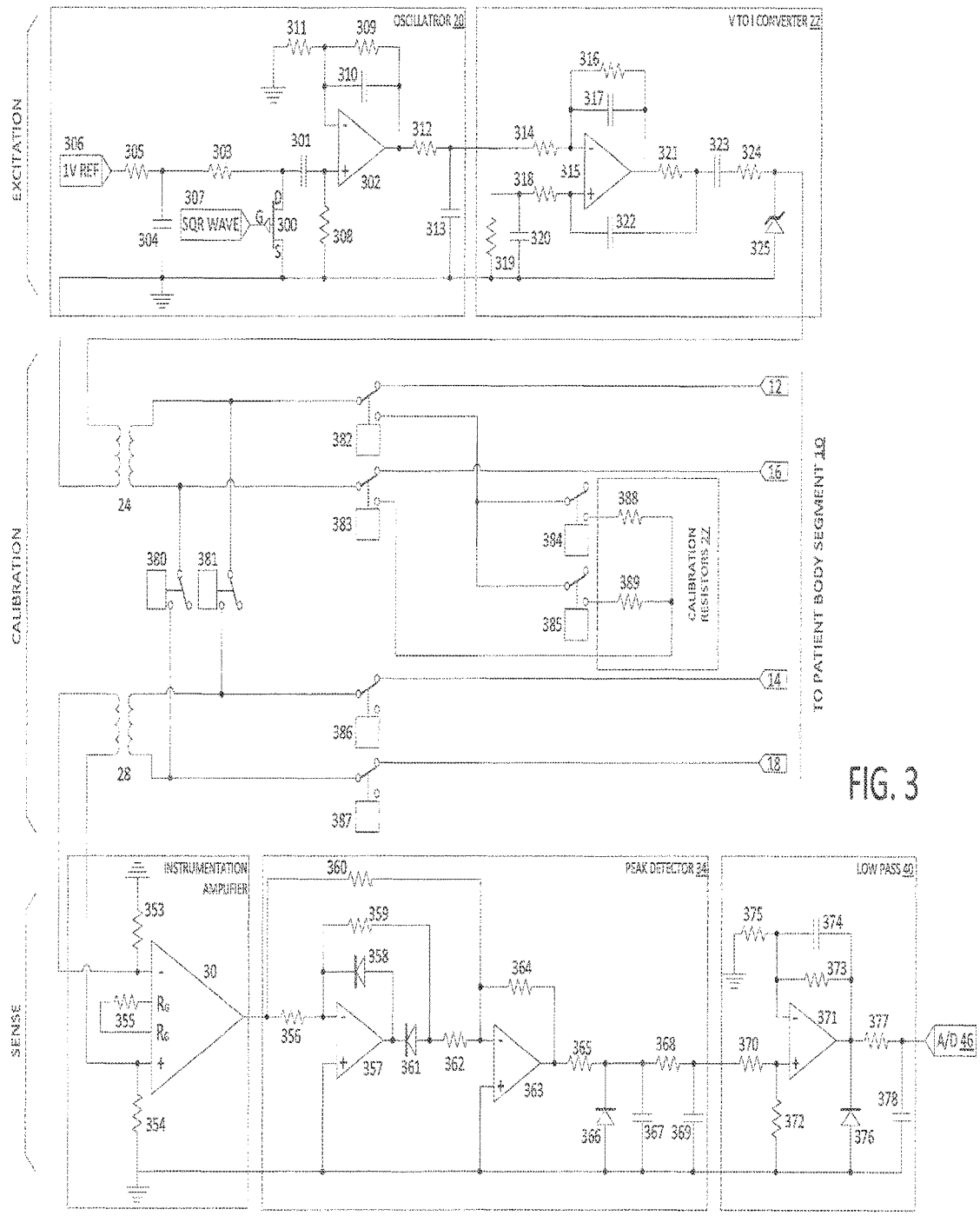
FIG. 3 is a schematic diagram of electrical circuitry of the current source, isolation, and sense circuitry utilized with the blood flow measuring device of FIG. 2.

FIG. 2 illustrates in block diagram form a preferred embodiment of the impedance plethysmograph of the present invention. An oscillator 20, which may be a field effect transistor stabilized oscillator, is provided. The output of oscillator 20 is converted from a voltage to a current by means of V to I converter 22. The output of converter 22 may preferably be a sine wave signal of frequency 20 kilohertz and amplitude of 1 milliamp. A more detailed schematic diagram of the oscillator 20 and converter 22 is shown in FIG. 3.

The output from the converter 22 is fed through an isolation transformer 24. As previously set forth, the outer patient electrodes 12 and 16 are connected to the secondary of isolation transformer 24.

The output from the inner patient electrodes 14 and 18 is connected to the primary of a second isolation transformer 28. The secondary windings of that isolation transformer 28 are connected to an instrumentation amplifier 30 which may be, for instance, an operational amplifier manufactured by Analog Devices, model number AD521AR, of gain 25. The output from the instrumentation amplifier 30 may be fed to a peak detector 34.

The output from the peak detector 34 is fed to a lowpass filter 40, which in this embodiment, is a 1st order active filter at 31 Hz to eliminate high frequency noise. The output from the lowpass filter 40 is a voltage which is proportional to the total tissue impedance, including the low magnitude phasic component. The output from the lowpass filter 40 may be fed to the input of an analog-to-digital (A/D) converter 46. The output of the A/D converter 46 may be fed to a computer 48.

Calibration resistors 27 are substituted for the electrodes and body segment during a calibration procedure that occurs before measurements are made. The calibration procedure is described below.

In an embodiment, all of the circuitry set forth in FIG. 2, with the exception of the computer 48, may preferably be powered from a power supply which supplies plus and minus 15 volts DC. Such a power supply is manufactured, for example, by Mean Well, and is designated as model RS-100.

Turning now to FIG. 3, an embodiment of a detailed circuit diagram of the oscillator 20 and voltage-to-current converter 22 is shown therein. The oscillator 20 is based upon a field effect transistor (FET) 300, which may preferably be a model number ZVN3306A, N-channel device. The drain of the FET 300 is connected through a capacitor 301 to the non-inverting input of an operational amplifier 302. The operational amplifier may be a model number LF353 manufactured by Texas Instruments. The source of the FET 300 is connected to ground. The drain of the FET 300 is connected to ground through resistor 303 and capacitor 304. Resistor 303 is connected through resistor 305 to 1V voltage reference 306, provided by a digital-to-analog converter, which may be a model number AD7804 manufactured by Analog Devices. The gate of the FET 300 is connected to a 20 KHz square wave output 307, generated by a digital signal processor, which may be a model number TMS320VC5501PGF manufactured by Texas Instruments. The non-inverting input of an operational amplifier 302 is connected to ground through resistor 308. The output of operational amplifier 302 is fed back to the inverting input of the operational amplifier 302 through resistor 309 and capacitor 310. The inverting input of the operational amplifier 302 is also connected to ground through resistor 311. The output of operational amplifier 302 is fed to ground through resistor 312 and capacitor 313. Thus, by appropriate selection of the values of the resistors and capacitors utilized in the oscillator circuit 20, a sine wave output of approximately 20 KHz is available at the output of the resistor 312.

The output from resistor 312 is fed through resistor 314 to the inverting input of a second operational amplifier 315, which functions as the primary element of the voltage-to-current converter 22. The operational amplifier 315 may be preferably a model number LF353 manufactured by Texas Instruments. The output of the operational amplifier 315 is fed back to the inverting input of the operational amplifier 315 through resistor 316 and capacitor 317. The non-inverting input is connected to ground through resistor 318 in series with resistor 319 and capacitor 320. The output of operational amplifier 315 is also fed back to its non-inverting input through resistor 321 and capacitor 322. The output of resistor 321 is connected to the cathode of a Transient Voltage Suppressor diode 325 through capacitor 323 and resistor 324. The diode 325 may preferably be a model number SD05 manufactured by Semtech. The anode of the diode 325 is connected to ground. The output from the cathode of the diode 325 is fed to the primary coil of the isolation transformer 24.

The secondary coil of isolation transformer 24 passes the 20 KHz excitation current through single-pole double-throw (SPDT) relays 382 and 383 onto body segment 10 via two electrodes 12 and 16. The resulting voltage in the limb is measured between a second pair of electrodes 14 and 18. That voltage is then passed through SPDT relays 386 and 387 into isolation transformer 28 and then instrumentation amplifier 30. The inverting and non-inverting inputs of instrumentation amplifier 30 are grounded via resistors 353 and 354, respectively. An appropriate resistor 355 is placed across gain inputs $R_G$, to ensure a voltage gain of 25.

The output of instrumentation amplifier 30 is fed into peak detector 34 based upon two operational amplifiers 357 and 363. The operational amplifiers may be preferably a model number LM318P manufactured by Texas Instruments. The signal from instrumentation amplifier 30 is connected into inverting inputs of operational amplifiers 357 and 363 via resistors 356 and 360, respectively. The non-inverting inputs of operational amplifiers 357 and 363 are grounded. The output of operational amplifier 357 is fed back into its inverting input via diode 358, and also via diode 361 and resistor 359 connected in series. Diodes 358 and 361 may be a model number 1N4148 manufactured by Fairchild Semiconductor™. The anode of diode 361 is connected to inverting input of operational amplifier 363 via resistor 362. The output of operational amplifier 363 is fed back into its inverting input via resistor 364. The output of operational amplifier 363 is connected to ground via resistor 365 and diode 366 (also model number 1N4148). The cathode of diode 366 is connected to ground via capacitor 367. The non-grounded terminal of capacitor 367 is connected to ground via resistor 368 and capacitor 369. By appropriate selection of the values of the resistors and capacitors utilized in the peak detector circuit 34, a voltage signal representing envelope of the sine wave is available at the output of the resistor 368.

That signal is then passed into a low pass filter 40, based upon operational amplifier 371, which may preferably be model TLE2141 manufactured by Texas Instruments. The signal passes through resistor 370 into non-inverting input of operational amplifier 371. The non-inverting input is connected to ground via resistor 372. The inverting input is connected to ground via resistor 375. The output of operational amplifier 371 is fed back into the inverting input via resistor 373 and capacitor 374 connected in parallel. The output of operational amplifier 371 is connected to ground via diode 376 (also model number 1N4148). The output of operational amplifier 371 is also connected to ground via resistor 377 and capacitor 378. The non-grounded terminal of capacitor 378 is connected to input of analog-to-digital converter 46. By appropriate selection of the values of the resistors and capacitors utilized in the low pass filter circuit 40, the voltage signal is low-pass filtered at the corner frequency of 31 Hz.

The eight single-pole double-throw (SPDT) relays (380 through 387) allow automated calibration and electrode check. The relays may preferably be model G5V-1 manufactured by Omron. The self-calibration is performed by first energizing relays 382 and 383, which connect excitation circuit to the calibration resistors 27, instead of the body segment 10. At the same time relays 386 and 387 are energized to disconnect sense circuit from body segment 10. Simultaneously, relays 380 and 381 are energized to connect sense circuit to the excitation circuit, so that the voltage drop across calibration resistors 27 can be measured. Two separate measurements are performed. The first measurement energizes relay 384, so that the voltage drop across resistor 388 of value 100 Ohm is obtained. The second measurement energizes both relay 384 and 385, so that the voltage drop is obtained across the parallel combination of resistors 388 and 389 (also 100 Ohm), which results in effective 50 Ohm resistance. The two resulting voltage points are then linearly interpolated to create a calibration curve allowing conversion between A/D converter voltage and resistance.

The automated electrode check is performed by energizing relays 380 and 381, which shorts each outer electrode to its adjacent inner electrode. This makes it possible to perform resistance measurements with only two electrodes connected to patient body segment 10. Four sets of measurements are then performed, with only two electrodes connected to the patient at a time, by energizing only two out of the four electrode relays 382, 383, 386 and 387. A short (low resistance), or an open (high resistance) reading in any of the measurements indicates a problem with electrode hardware, or electrode preparation, which is communicated to the user via display.

Figure 4:
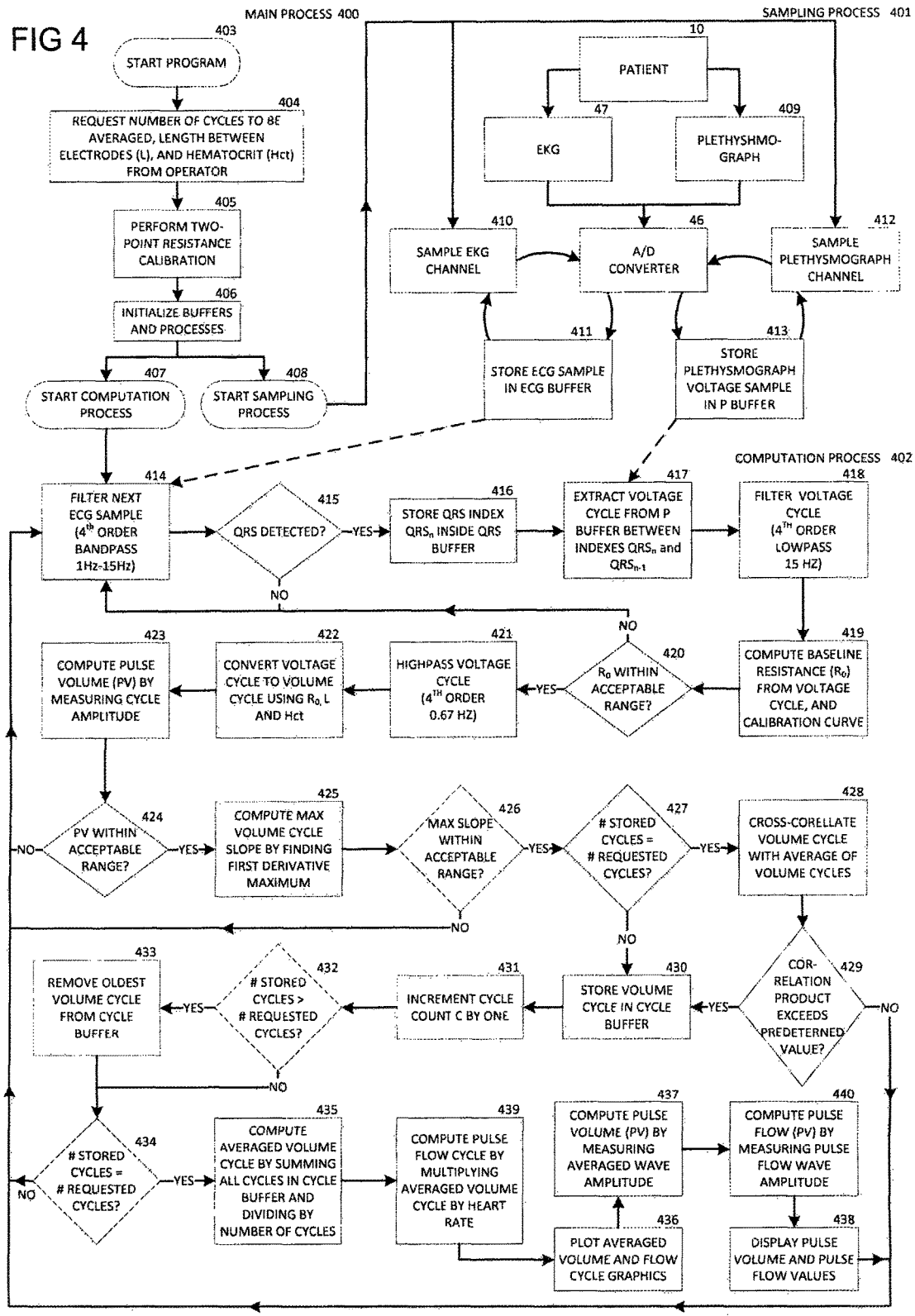
FIG. 4 is a flowchart illustrating a program utilized by the digital computer as used in the present invention.

As shown in FIG. 2, the plethysmogram signal output from lowpass filter 40 and the ECG signal 47 may all be fed continuously to the analog-to-digital converter 46. Turning now to FIG. 4, the program contained in the computer 48 is composed of three processes: a main process 400, a sampling process 401 and a computation process 402. The program starts 403, and requests the number of cycles to be averaged, the length between the electrodes (L) and the hematocrit (Hct) from the operator 404. The program then performs a two-point resistance calibration 405 by substituting resistors 27 (FIG. 2) for the electrodes and body segment. The buffers and processes are then initialized 406. The main process 400 then starts a sampling process 408, which is responsible for continuously sampling ECG 47 and plethysmograph 409 signals connected to A/D converter 46 (FIG. 2). The ECG samples are stored inside ECG buffer 411 and the plethysmograph samples are stored inside P buffer 413.

The main process 400 also starts a computation process 402, which is responsible for processing the data being continuously obtained by the sampling process. Each incoming ECG sample is digitally filtered using a $4^{th}$ order bandpass Butterworth filter with lower and upper cutoff frequencies of 1 Hz and 15 Hz respectively (414). The program then determines whether a QRS complex has occurred in the ECG signal 415. If not, the program processes the next ECG sample 414. If the proper conditions have been met to identify a new QRS complex, the program stores the index $QRS_n$ of the ECG sample at which the detection was made 416. Since plethysmograph 409 and ECG 47 signals are sampled simultaneously by the A/D converter 46, the sample indexes correspond to the same point in time for both channels. That allows the program to identify and extract a single voltage cycle 417 from voltage samples stored in P buffer 413. The extracted samples are bound by the last two QRS indexes, starting at $QRS_{n-1}$ and ending at $QRS_n$.

The extracted voltage cycle is then digitally filtered using a $4^{th}$ order lowpass Butterworth filter with a cutoff frequency of 15 Hz (418), to eliminate high frequency noise. The program then calculates baseline resistance $R_O$ 419 based on the filtered voltage, and the calibration curve obtained in step 405. The program then determines whether the baseline resistance is within a predetermined acceptable range 420. If it isn't, the program processes the next ECG sample 414. If it is, the program then filters the voltage points using a $4^{th}$ order highpass Butterworth filter with a cutoff frequency of 0.67 Hz (421), to extract the phasic component of tissue impedance. The filtered points are converted from voltage into physiologic units of volume using baseline resistance $R_O$, electrode length (L) and hematocrit (Hct) values 422. This is done using the Nyboer equation:

$$\Delta V = \rho (L/Z_o)^2 \Delta Z$$

where $\Delta V$ is the change in volume, $\rho$ is the blood resistivity, L is the length between the inner electrodes, $Z_o$ is the baseline impedance and $\Delta Z$ is the change in impedance.

The program then identifies and computes the peak-to-peak value (PV) of the pulsatile volume cycle 423. The program then determines whether the PV number exceeds a predetermined acceptable range 424. If it does, the program processes the next ECG sample 414. If it does not, the program then calculates maximum slope of the volume cycle by finding the maximum of the absolute values of first derivative points 425.

The program then determines whether the maximum slope is within a predetermined acceptable range 426. If it isn't, the program processes the next ECG sample 414. If it is, it is determined if the number of stored cycles is equal to the number of requested cycles 427. If the number of requested cycles does not equal the number of stored cycles, then the average is not complete and the program stores the current volume cycle in the cycle buffer 430. If the number of requested cycles equals the number of stored cycles, then an averaged waveform exists. The averaged waveform is compared to the current cycle using the cross-correlation technique 428. In the cross-correlation technique, the two waveforms to be compared are first high pass filtered such that they have an equal area above and below the baseline. The waveforms are then sampled, for example 200 times at equal intervals. The value of the waveforms at each sampled interval is multiplied and the results of those multiplications are summed to provide a "correlation product." If the correlation product exceeds a predetermined value 429, then the current waveform is deemed acceptable and it is stored in the cycle buffer 430. If the correlation product does not exceed the predetermined value then the program processes the next ECG sample 414.

After a volume cycle is stored 430, the cycle count C is incremented by one 431. The program then determines whether the number of stored cycles is greater than the number of cycles requested 432. If it is, the oldest volume cycle is removed from cycle buffer 433. The program then checks if the number of stored cycles is equal to the number of cycles requested 434. If it isn't, the program processes the next ECG sample 414. If it is, the program computes averaged volume cycle by summing all stored cycles and dividing them by their count 435.

The averaged pulse flow cycle is computed by multiplying the averaged volume cycle by the heart rate 439.

The averaged volume cycle and the averaged pulse flow cycle are then displayed on a suitable output device 436 (not shown). The program then identifies and computes the peak-to-peak value of the pulsatile volume curve 437 and the pulse flow curve 440. These values are then displayed on a suitable output device 438 (not shown). The program then processes next ECG sample 414.

Figure 5:
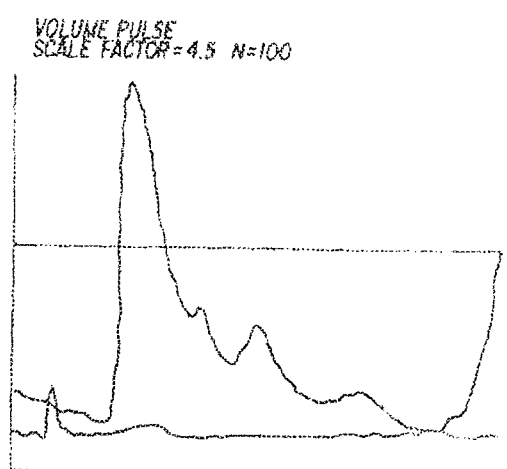
FIG. 5 is a graph illustrating a volume pulse signal obtained by the present invention.
Figure 6:
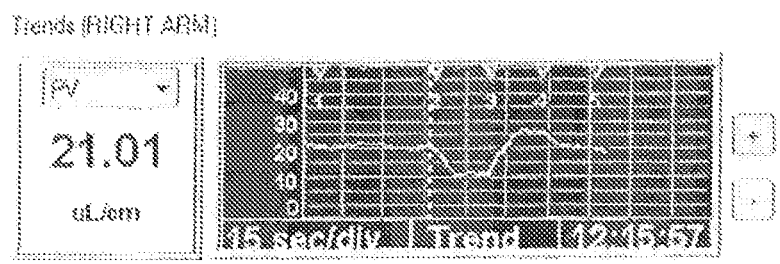
FIG. 6 is a graph illustrating pulsatile volume versus time with pulse volume measured in microliters per centimeter.

The desired volume pulse graph is shown in FIG. 5. The program provides continuous measurements and/or graphic representation of pulsatile volume as shown in FIG. 6. In FIG. 6, the x axis is time and the y-axis is the pulse volume measured in microliters per centimeter. A Valsalva maneuver (increase of intrathoracic pressure against a closed glottis), indicated at a point 2, is shown to decrease the pulsatile volume transiently. After the Valsalva is released, the pulse volume increases as indicated at point 3. It then overshoots the baseline as indicated at point 4 before finally returning to baseline as indicated at point 5.

In view of the foregoing, it should be apparent that there is provided by the present invention an impedance plethysmograph in which a high signal-to-noise ratio of the output signal measured from a body segment is achieved. In addition, by means of a digital computer the outputs from the plethysmograph are analyzed and clarified such that the effects of the reduced signal-to-noise ratio are further enhanced. Furthermore, the pulsatile and ECG waveforms are stored in buffers, so that all waveforms are available for processing.

Figure 7:
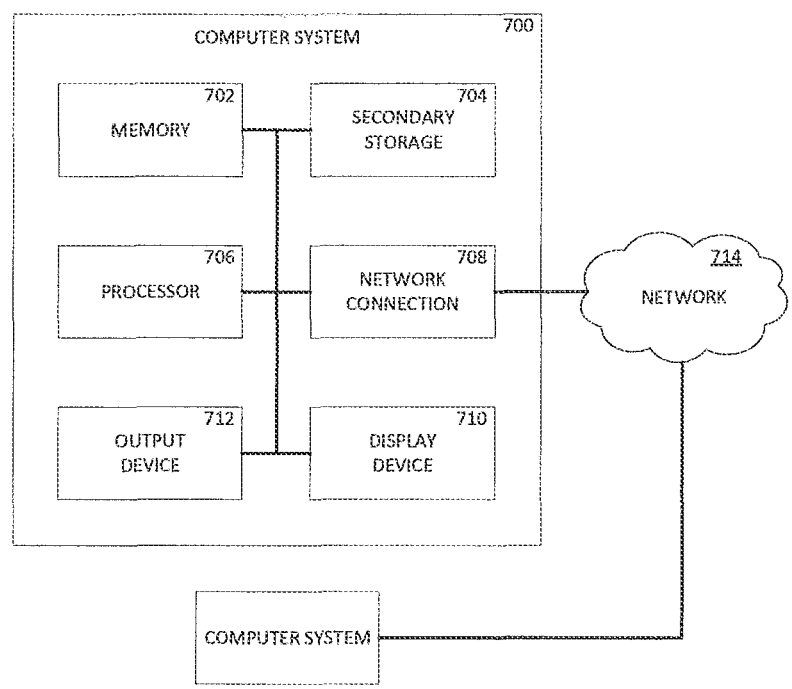
FIG. 7 is block diagram illustrating exemplary hardware components for implementing embodiments of a system and method for impedance plethysmography using concurrent processing and template matching techniques.

With reference now to FIG. 7, there is shown a block diagram of exemplary hardware that may be used to provide the system and perform the method for computations and communication. Exemplary hardware implementation of the system may include multiple computing devices 700 (e.g., computing system N). Computing devices 700 may be, e.g., blade servers or other stack servers. For example, each component shown in the system may be implemented as software running on one or more computing devices 700. Alternatively, components and functionality of each may be combined and implemented as software running on a single computing device 700. Furthermore, steps of the method may be implemented as software modules executed on one or more computing devices 700.

Computing device 700 may include a memory 702, a secondary storage device 704, a processor 706, and a network connection 708. Computing device 700 may be connected a display device 710 (e.g., a terminal connected to multiple computing devices 700) and output device 712. Memory 702 may include RAM or similar types of memory, and it may store one or more applications (e.g., software for performing functions or including software modules described herein) for execution by processor 706. Secondary storage device 704 may include a hard disk drive, DVD-ROM drive, or other types of non-volatile data storage. Processor 706 executes the applications, which are stored in memory 702 or secondary storage 704, or received from the Internet or other network 714. Network connection 708 may include any device connecting computing device 700 to a network 714 and through which information is received and through which information (e.g., analysis results) is transmitted to other computing devices. Network connection 708 may include network connection providing connection to internal enterprise network, network connection provided connection to Internet or other similar connection. Network connection 708 may also include bus connections providing connections to other computing devices 700 in the system (e.g., other servers in server stack).

Display device 710 may include any type of device for presenting visual information such as, for example, a computer monitor or flat-screen display. Output device 712 may include any type of device for presenting a hard copy of information, such as a printer, and other types of output devices include speakers or any device for providing information in audio form. Computing device 700 may also include input device, such as keyboard or mouse, permitting direct input into computing device 700.

Computing device 700 may store a database structure in secondary storage 704 for example, for storing and maintaining information needed or used by the software stored on computing device 700. Also, processor 702 may execute one or more software applications in order to provide the functions described in this specification, specifically in the methods described above, and the processing may be implemented in software, such as software modules, for execution by computers or other machines. The processing may provide and support web pages and other user interfaces.

Although computing device 700 is depicted with various components, one skilled in the art will appreciate that the servers can contain additional or different components. In addition, although aspects of an implementation consistent with the above are described as being stored in memory, one skilled in the art will appreciate that these aspects can also be stored on or read from other types of computer program products or computer-readable media. The computer-readable media may include instructions for controlling a computer system, such as computing device 700, to perform a particular method.

More generally, even though the present disclosure and exemplary embodiments are described above with reference to the examples according to the accompanying drawings, it is to be understood that they are not restricted thereto. Rather, it is apparent to those skilled in the art that the disclosed embodiments can be modified in many ways without departing from the scope of the disclosure herein. Moreover, the terms and descriptions used herein are set forth by way of illustration only and are not meant as limitations. Those skilled in the art will recognize that many variations are possible within the spirit and scope of the disclosure as defined in the following claims, and their equivalents, in which all terms are to be understood in their broadest possible sense unless otherwise indicated.

The invention claimed is:

1. A method for measuring the impedance and impedance changes in a body segment, the method comprising:
    acquiring a new ECG waveform;
    detecting QRS complexes from the new ECG waveform;
    storing a previously acquired ECG waveform in at least one ECG buffer;
    acquiring a plurality of new impedance waveforms;
    storing the plurality of previously acquired impedance waveforms in at least one plethysmograph buffer;
    extracting the previously acquired ECG waveform stored in the at least one ECG buffer;
    extracting the plurality of previously acquired impedance waveforms stored in the at least one plethysmograph buffer; and
    averaging the plurality of previously acquired impedance waveforms to obtain a single waveform representative of the average of the plurality of previously acquired impedance waveforms;
    wherein the acquiring the new ECG waveform, the acquiring the plurality of new impedance waveforms, the extracting the previously acquired ECG waveform, and the extracting the plurality of previously acquired impedance waveforms are performed concurrently.

2. The method of claim 1, further comprising determining an amplitude of the single waveform.

3. The method of claim 2, further comprising displaying the single waveform and its amplitude.

4. The method of claim 3, wherein the displaying the single waveform is performed concurrently with the acquiring the new ECG waveform and the acquiring the plurality of new impedance waveforms.

5. The method of claim 3, wherein the measuring the single waveform is performed concurrently with the acquiring the new ECG waveform and the acquiring the plurality of new impedance waveforms.

6. The method of claim 1, further comprising determining pulse volume from the single waveform.

7. The method of claim 1, wherein the averaging is performed via utilizing the QRS complexes as a gating signal.

8. The method of claim 1, wherein, prior to the averaging, the plurality of previously acquired impedance waveforms used to obtain the single waveform are analyzed to determine whether they are acceptable for the averaging.

9. A method for measuring the impedance and impedance changes in a body segment, the method comprising:
    acquiring a new ECG waveform;
    detecting QRS complexes from the new ECG waveform;
    storing a previously acquired ECG waveform in at least one ECG buffer;
    acquiring a plurality of new impedance waveforms;
    storing the plurality of previously acquired impedance waveforms in at least one plethysmograph buffer;
    extracting the previously acquired ECG waveform stored in the at least one ECG buffer;
    extracting the plurality of previously acquired impedance waveforms stored in the at least one plethysmograph buffer; and
    averaging the plurality of previously acquired impedance waveforms to obtain a single waveform representative of the average of the plurality of previously acquired impedance waveforms;
    wherein the acquiring the new ECG waveform, the acquiring the plurality of new impedance waveforms, and the averaging the plurality of previously acquired impedance waveforms are performed concurrently.

10. The method of claim 9, further comprising determining an amplitude of the single waveform.

11. The method of claim 10, further comprising displaying the single waveform and its amplitude.

12. The method of claim 11, wherein the averaging the plurality of previously acquired impedance waveforms and the displaying the single waveform are performed concurrently.

13. The method of claim 11, wherein the measuring the single waveform is performed concurrently with the acquiring the new ECG waveform and the acquiring the plurality of new impedance waveforms.

14. The method of claim 9, further comprising determining pulse volume from the single waveform.

15. The method of claim 9, wherein the averaging is performed via utilizing the QRS complexes as a gating signal.

16. The method of claim 9, wherein, prior to the averaging, the plurality of previously acquired impedance waveforms used to obtain the single waveform are analyzed to determine whether they are acceptable for the averaging.

17. A system that measures the impedance and impedance changes in a body segment, the system comprising:
    an ECG device that acquires a new ECG waveform, wherein QRS complexes are detected from the new ECG waveform;
    at least one ECG buffer that stores a previously acquired ECG waveform;
    a plethysmograph that acquires a plurality of new impedance waveforms;
    at least one plethysmograph buffer that stores a plurality of previously acquired impedance waveforms;
    wherein the previously acquired ECG waveform stored in the at least one ECG buffer is extracted;
    wherein the plurality of previously acquired impedance waveforms stored in the at least one plethysmograph buffer are extracted;
    wherein the plurality of previously acquired impedance waveforms are averaged to obtain a single waveform representative of the average of the plurality of previously acquired impedance waveforms; and
    wherein the acquisition of the new ECG waveform, the acquisition of the plurality of new impedance waveforms, and the averaging the plurality of previously acquired impedance waveforms are performed concurrently.

18. The system of claim 17, wherein the single waveform comprises an amplitude.

19. The system of claim 18, further comprising a display device that displays the single waveform and its amplitude.

20. The system of claim 19, wherein the averaging the plurality of previously acquired impedance waveforms and the displaying the single waveform are performed concurrently.

21. The system of claim 19, wherein the measurement of the single waveform is performed concurrently with the acquisition of the new ECG waveform and the acquisition of the plurality of new impedance waveforms.

22. The system of claim 17, wherein pulse volume is determined from the single waveform.

23. The system of claim 17, wherein the QRS complexes are utilized as a gating signal to obtain the single waveform from the average of the plurality of previously acquired impedance waveforms.

24. The system of claim 17, wherein, prior to the averaging, the plurality of previously acquired impedance waveforms used to obtain the single waveform are analyzed to determine whether they are acceptable for the averaging.

25. A system that measures the impedance and impedance changes in a body segment, the system comprising:
    an ECG device that acquires a new ECG waveform, wherein QRS complexes are detected from the new ECG waveform;
    at least one ECG buffer that stores a previously acquired ECG waveform;
    a plethysmograph that acquires a plurality of new impedance waveforms;
    at least one plethysmograph buffer that stores a plurality of previously acquired impedance waveforms;
    wherein the previously acquired ECG waveform stored in the at least one ECG buffer is extracted;
    wherein the plurality of previously acquired impedance waveforms stored in the at least one plethysmograph buffer are extracted;
    wherein the plurality of previously acquired impedance waveforms are averaged to obtain a single waveform representative of the average of the plurality of previously acquired impedance waveforms; and wherein the acquisition of the new ECG waveform, the acquisition of the plurality of new impedance waveforms, the extraction of the previously acquired ECG waveform, and the extraction of the plurality of previously acquired impedance waveforms are performed concurrently.

26. The system of claim 25, wherein, prior to the averaging, the plurality of previously acquired impedance waveforms used to obtain the single waveform are analyzed to determine whether they are acceptable for the averaging.

* * * * *